US008663702B2

(12) United States Patent
Takebe et al.

(10) Patent No.: US 8,663,702 B2
(45) Date of Patent: *Mar. 4, 2014

(54) MICROPARTICLES, MICROPARTICLE DISPERSION AND METHOD AND APPARATUS FOR PRODUCING THE SAME

(75) Inventors: Gen Takebe, Hamamatsu (JP); Tomonori Kawakami, Hamamatsu (JP); Tokio Takagi, Hamamatsu (JP); Mitsuo Hiramatsu, Hamamatsu (JP)

(73) Assignee: Hamamatsu Photonics K.K., Hamamatsu-shi, Shizuoka (JP)

(*) Notice: Subject to any disclaimer, the term of this patent is extended or adjusted under 35 U.S.C. 154(b) by 693 days.

This patent is subject to a terminal disclaimer.

(21) Appl. No.: 12/295,666

(22) PCT Filed: Mar. 19, 2007

(86) PCT No.: PCT/JP2007/055533
§ 371 (c)(1),
(2), (4) Date: Feb. 2, 2009

(87) PCT Pub. No.: WO2007/116632
PCT Pub. Date: Oct. 18, 2007

(65) Prior Publication Data
US 2009/0142402 A1  Jun. 4, 2009

(30) Foreign Application Priority Data
Apr. 7, 2006  (JP) ................. P2006-106523

(51) Int. Cl.
*A61K 9/10* (2006.01)
*B02C 23/36* (2006.01)
*B29B 9/10* (2006.01)

(52) U.S. Cl.
USPC .................... 424/490; 264/5; 241/46.01

(58) Field of Classification Search
None
See application file for complete search history.

(56) References Cited

U.S. PATENT DOCUMENTS

| 2006/0057219 | A1* | 3/2006 | Nagasaki et al. ............. 424/490 |
| 2007/0114306 | A1* | 5/2007 | Kawakami et al. ............. 241/1 |
| 2007/0152360 | A1* | 7/2007 | Kawakami et al. ............. 264/5 |
| 2009/0081301 | A1 | 3/2009 | Takebe et al. |
| 2009/0087460 | A1 | 4/2009 | Takebe et al. |
| 2011/0285043 | A1 | 11/2011 | Takebe et al. |
| 2011/0306564 | A1 | 12/2011 | Takebe et al. |

FOREIGN PATENT DOCUMENTS

| JP | 60-115515 | 6/1985 |
| JP | 2002-128660 | 5/2002 |
| JP | 2003-342168 | 12/2003 |
| JP | 2004-267918 | 9/2004 |
| JP | 2005-8524 | 1/2005 |
| JP | 2005-177596 | 7/2005 |
| JP | 2005-238342 | 9/2005 |
| WO | WO 03099260 A1 * | 12/2003 |
| WO | 2005/049213 | 6/2005 |
| WO | WO 2005058480 A2 * | 6/2005 |

OTHER PUBLICATIONS

Kawakami (WO 2005/049213 published on Jun. 2, 2005.*
U.S. Office Action dated Mar. 2, 2011 that issued in U.S. Appl. No. 12/235,825 including a Double Patenting Rejection on pp. 5-7.
U.S. Office Action dated Jan. 31, 2011 that issued in U.S. Appl. No. 12/235,811 including a Double Patenting Rejection on pp. 10-12.
Final Office Action dated Sep. 15, 2011 that issued in U.S. Appl. No. 12/235,811 including a double patenting rejection on pp. 9-10.
Office Action dated Nov. 10, 2011 that issued in U.S. Appl. No. 13/195,373 including double patenting rejections on pp. 9-11.
Office Action dated Oct. 28, 2011 that issued in U.S. Appl. No. 13/217,687 including double patenting rejections on pp. 6-9.
U.S. Office Action dated Jun. 7, 2012 that issued in U.S. Appl. No. 13/195,373 including Double Patenting Rejections on pp. 13-15.
U.S. Office Action dated Oct. 30, 2012 that issued in U.S. Appl. No. 13/195,373 including Double Patenting Rejections on pp. 12-13.
U.S. Office Action dated May 7, 2012 that issued in U.S. Appl. No. 12/235,825 including Double Patenting Rejections on pp. 8-11.
U.S. Office Action dated Dec. 7, 2012 that issued in U.S. Appl. No. 12/235,825 including Double Patenting Rejections on pp. 9-11.

* cited by examiner

*Primary Examiner* — Robert A Wax
*Assistant Examiner* — H. Sarah Park
(74) *Attorney, Agent, or Firm* — Drinker Biddle & Reath LLP

(57) ABSTRACT

A method and an apparatus enabling manufacture of a microparticle dispersion liquid at high efficiency in a short time while suppressing drug degradation, etc., are provided. In a dissolving step, a poorly soluble drug and a dispersion stabilizer are dissolved in a volatile organic solvent in a container 13. In a fixing step following the dissolving step, the organic solvent, contained in a solution, is eliminated by evaporation, a pellet-form residue 1 is obtained by the organic solvent elimination, and the residue 1 is fixed on an inner wall of the container 13. In a water injecting step following the fixing step, water 2 is injected into an interior of the container 13. In an irradiating step following the water injecting step, laser light 1, emitted from a laser light source 11, is irradiated on the residue 1 fixed on the inner wall of the container 13, and the residue 1 is thereby pulverized and made into microparticles and a microparticle dispersion liquid, constituted of the microparticles being dispersed in the water 2, is manufactured. The microparticles contain the poorly soluble drug and the dispersion stabilizer.

8 Claims, 14 Drawing Sheets ized into highly dispersed scattered matter, and the highly dispersed scattered matter is recovered by the solvent to obtain ultrafine microparticles of an organic compound. With the invention disclosed in the Patent Document 2, a solution is prepared by dispersing and dissolving a block copolymer, containing a hydrophilic segment and a hydrophobic segment, and a poorly water-soluble drug in a volatile organic solvent, the organic solvent is eliminated from the solution, and a residue obtained by elimination of the organic solvent is stirred and thereby uniformly dispersed in water at a temperature of no more than 30° C. to manufacture a formulation containing polymer micelles encapsulating the drug.

Patent Document 1: Japanese Published Unexamined Patent Application No. 2005-238342
Patent Document 2: Japanese Published Unexamined Patent Application No. 2003-342168

MICROPARTICLES, MICROPARTICLE DISPERSION AND METHOD AND APPARATUS FOR PRODUCING THE SAME

TECHNICAL FIELD

The present invention relates to microparticles, containing a poorly soluble drug and a dispersion stabilizer, a microparticle dispersion liquid, with which the microparticles are dispersed in water, an orally administered formulation and an injection formulation, containing the microparticles, and a method and an apparatus for manufacturing the microparticle dispersion liquid.

BACKGROUND ART

In the recent development of new medical drugs, combinatorial chemistry methods have been adopted in synthesizing candidate compounds. Combinatorial chemistry is the art of adopting combinations to synthesize a wide variety of compounds in a short time at one time. Compounds obtained by this method have a solubility problem in many cases. That is, in many cases, even if a compound is found to have excellent physiological activity in itself, if the compound has a property of being difficult to dissolve in water, development of the compound is abandoned. Even with compounds obtained by extraction from natural products, various organic syntheses are carried out and structural optimization is performed to improve solubility. Some medical drugs already on the market are also low in solubility. With such drugs, a drug absorption amount varies within an individual patient and varies among individuals, and this places a large burden in terms of control of levels in blood, etc. on both a physician using a drug and a patient on whom the drug is used.

Microparticle formulations have been received attention as a solution to the above problems. With a microparticle formulation, poorly soluble drug particles that are made no more than a micrometer in size are dispersed in water with stability. By using a microparticle formulation, a drug can be increased in absorption rate and amount in a living body. Reduction in variation of absorption amount within an individual patient and among individuals and increase in effective availability with respect to a dose can also be anticipated. Inventions of methods for manufacturing such microparticle formulations are disclosed in the following Patent documents 1 and 2.

With the invention disclosed in the Patent Document 1, ultrashort pulse laser light is irradiated on organic bulk crystals dispersed in a solvent to induce ablation by nonlinear absorption and thereby pulverize the organic bulk crystals into highly dispersed scattered matter, and the highly dispersed scattered matter is recovered by the solvent to obtain ultrafine microparticles of an organic compound. With the invention disclosed in the Patent Document 2, a solution is prepared by dispersing and dissolving a block copolymer, containing a hydrophilic segment and a hydrophobic segment, and a poorly water-soluble drug in a volatile organic solvent, the organic solvent is eliminated from the solution, and a residue obtained by elimination of the organic solvent is stirred and thereby uniformly dispersed in water at a temperature of no more than 30° C. to manufacture a formulation containing polymer micelles encapsulating the drug.

DISCLOSURE OF THE INVENTION

Problems to be Solved by the Invention

However, with the invention disclosed in Patent Document 1, because the organic bulk crystals to be pulverized are in a state of being dispersed in a solvent, the irradiation of laser light on the organic bulk crystals is incidental and low in processing efficiency. Also because the ultrashort pulse laser light must be irradiated to induce ablation in the dispersed organic bulk crystals, an extremely high laser light irradiation intensity is required and lowering of pharmacological activity due to degradation, etc., of the drug is predicted. Meanwhile, with the invention disclosed in Patent Document 2, combined application of stirring and ultrasonic treatment for no less than five hours is required to obtain the drug-encapsulating polymer micelles, and thus a troublesome operation of long duration is required.

The present invention has been made to resolve the above issues and an object thereof is to provide a method and an apparatus enabling manufacture of a microparticle dispersion liquid at high efficiency in a short time while suppressing drug degradation, etc.

Means for Solving the Problem

A method for manufacturing a microparticle dispersion liquid according to the present invention includes: (1) a dissolving step of dissolving a poorly soluble drug and a dispersion stabilizer in a volatile organic solvent; (2) a fixing step of performing elimination by evaporation of the organic solvent, contained in a solution obtained in the dissolving step, and fixing a residue, obtained by the organic solvent elimination, on an inner wall of a container; (3) a water injecting step of injecting water into an interior of the container after the fixing step; and (4) an irradiating step of irradiating light on the residue fixed on the inner wall of the container after the water injecting step to manufacture a liquid having microparticles, containing the poorly soluble drug and the dispersion stabilizer, dispersed in water.

A single container may be used throughout the entirety of the dissolving steps fixing step, water injecting step, and irradiating step. The container used in the steps until the residue is obtained and the container used in the steps from the fixing of the residue onward may be separate from each other.

With the present microparticle dispersion liquid manufacturing method, the poorly soluble drug and the dispersion stabilizer are dissolved in the volatile organic solvent in the dissolving step. Then, in the subsequent fixing step, the organic solvent, contained in the solution obtained in the dissolving step, is eliminated by evaporation, and the residue, obtained by the organic solvent elimination, is fixed on the inner wall of the container. Water is then injected into the interior of the container in the injecting step that follows. Then, in the irradiating step, light is irradiated on the residue, fixed on the inner wall of the container, to manufacture the liquid having the microparticles, containing the poorly soluble drug and the dispersion stabilizer, dispersed in water.

With the microparticle dispersion liquid manufacturing method according to the present invention, preferably in the irradiating step, the light is irradiated from outside a region of the inner wall of the container on which the residue is fixed, and the irradiated light is made to propagate in an order of the container, the residue, and the water. Microparticles are thereby formed near an interface of the residue and the water and the microparticles become immediately dispersed in the water. Because the irradiation of the light on the interface is constantly performed via the residue, even when a high concentration of the microparticles is contained in the water, the microparticle formation is not lowered in efficiency and the microparticles are formed at a fixed efficiency.

Preferably with the microparticle dispersion liquid manufacturing method according to the present invention, light of a wavelength of no less than 900 nm is irradiated on the residue in the irradiating step. By light of such wavelength being irradiated on the residue, photodegradation of the drug contained in the residue can be suppressed further.

Preferably with the microparticle dispersion liquid manufacturing method according to the present invention, light of a wavelength of low absorbance with respect to the residue is irradiated in the irradiating step. In this case, light absorption by the residue is low and the light can arrive at high efficiency at the interface of the residue and the water.

Preferably with the microparticle dispersion liquid manufacturing method according to the present invention, both or either of an intensity and a duration of light irradiation on the residue are or is adjusted in the irradiating step to control a particle diameter of the microparticles. Preferably with the microparticle dispersion liquid manufacturing method according to the present invention, the irradiated region or the interior of the container is maintained at a fixed temperature during light irradiation on the residue in the irradiating step. A particle diameter of the microparticles formed by light irradiation is thereby stabilized.

Preferably with the microparticle dispersion liquid manufacturing method according to the present invention, a sealed container is used as the container and the dissolving step, the fixing step, the water injecting step, and the irradiating step are performed in a sterilized state. Or, the dissolving step may be performed under a non-sterilized state and after filter sterilization of the solution, the fixing step, the water injecting step, and the irradiating step may be performed in a sterilized state. That is, because the present invention is a simple method of simply irradiating light from an exterior of the container, it can be put into practice even in a sealed container and an injectable product can also be manufactured readily in a sterilized state.

Preferably with the microparticle dispersion liquid manufacturing method according to the present invention, a container, having a recess in the inner wall for fixing the residue, is used as the container. The residue can thereby be positioned at the recess, which is a constantly fixed position with respect to an outer wall of the container, and adjustment of a light irradiating position is facilitated.

Preferably with the microparticle dispersion liquid manufacturing method according to the present invention, a container, having a function of a syringe, is used as the container. This provides a merit of enabling rapid injection of the microparticle dispersion liquid immediately after manufacture.

Preferably with the microparticle dispersion liquid manufacturing method according to the present invention, the dispersion stabilizer is a high molecular weight polymer or a surfactant, and the organic solvent is preferably a low toxicity alcohol.

A microparticle dispersion liquid manufacturing apparatus according to the present invention includes: a container, in which a poorly soluble drug and a dispersion stabilizer are dissolved in a volatile organic solvent, a residue, obtained by elimination by evaporation of the organic solvent contained in the solution, is fixed on an inner wall, and water is injected into an interior; and a light source, irradiating light on the residue fixed on the inner wall of the container; and a liquid, having microparticles, containing the poorly soluble drug and the dispersion stabilizer, dispersed in water, is manufactured by irradiation of the light on the residue by the light source.

With the present microparticle dispersion liquid manufacturing apparatus, the poorly soluble drug and the dispersion stabilizer are dissolved in the volatile organic solvent, the residue, obtained by elimination by evaporation of the organic solvent contained in the solution, is fixed on the inner wall of the container, and water is injected into the interior of the container. The light from the light source is then irradiated on the residue fixed on the inner wall of the container, and the liquid, having the microparticles, containing the poorly soluble drug and the dispersion stabilizer, dispersed in water, is thereby manufactured.

Preferably with the microparticle dispersion liquid manufacturing apparatus according to the present invention, the light is irradiated by the light source from outside a region of the inner wall of the container on which the residue is fixed, and the irradiated light is made to propagate in an order of the container, the residue, and the water. Microparticles are thereby formed near an interface of the residue and the water and the microparticles become immediately dispersed in the water. Because the irradiation of the light on the interface is constantly performed via the residue, even when a high concentration of the microparticles is contained in the water, the microparticle formation is not lowered in efficiency and the microparticles are formed at a fixed efficiency.

Preferably with the microparticle dispersion liquid manufacturing apparatus according to the present invention, the light source irradiates light of a wavelength of no less than 900 nm on the residue. By light of such wavelength being irradiated on the residue, photodegradation of the drug contained in the residue can be suppressed further.

Preferably with the microparticle dispersion liquid manufacturing apparatus according to the present invention, the light source irradiates light of a wavelength of low absorbance with respect to the residue. In this case, light absorption by the residue is low and the light can arrive at high efficiency at the interface of the residue and the water.

Preferably the microparticle dispersion liquid manufacturing apparatus according to the present invention further includes: an irradiation light controller, controlling both or either of an intensity and a duration of light irradiation on the residue by the light source. Preferably the microparticle dispersion liquid manufacturing apparatus according to the present invention further includes: a temperature controller, maintaining the irradiated region or the interior of the container at a fixed temperature during the light irradiation on the residue by the light source. A particle diameter of the microparticles formed by light irradiation is thereby stabilized.

Preferably with the microparticle dispersion liquid manufacturing apparatus according to the present invention, the container is a sealed container that can be maintained in a sterilized state. That is, because the present invention provides a simple method of simply irradiating light from an exterior of the container, it can be put into practice even in a sealed container and an injectable product can also be manufactured readily in a sterilized state.

Preferably with the microparticle dispersion liquid manufacturing apparatus according to the present invention, the container has a recess in the inner wall for fixing the residue. The residue can thereby be positioned at the recess, which is a constantly fixed position with respect to an outer wall of the container, and adjustment of a light irradiating position is facilitated.

Preferably with the microparticle dispersion liquid manufacturing apparatus according to the present invention, the container has a function of a syringe. This provides a merit of enabling rapid injection of the microparticle dispersion liquid immediately after manufacture.

A microparticle dispersion liquid according to the present invention is manufactured by the microparticle dispersion liquid manufacturing method according to the present invention and has microparticles, containing a poorly soluble drug and a dispersion stabilizer, dispersed in water. Microparticles according to the present invention are manufactured from the microparticle dispersion liquid according to the present invention and contain a poorly soluble drug and a dispersion stabilizer. Lyophilized microparticles according to the present invention are manufactured by lyophilizing the microparticle dispersion liquid according to the present invention or a liquid, containing the microparticles according to the present invention. An orally administered formulation according to the present invention contains the microparticle dispersion liquid, the microparticles, or the lyophilized microparticles according to the present invention. An injection formulation according to the present invention contains the microparticle dispersion liquid according to the present invention or a dispersion liquid obtained by resuspending the microparticles or the lyophilized microparticles according to the present invention in water.

Effects of the Invention

According to the present invention, a microparticle dispersion liquid can be manufactured at high efficiency in a short time while suppressing drug degradation, etc.

DESCRIPTION OF THE REFERENCE NUMERALS

1 Residue
2 Water
10 Microparticle dispersion liquid manufacturing apparatus
11 Laser light source
12 Irradiation light controller
13, 13A, 13B Container
14 Temperature controller
131 Recess
132 Injection needle
L Laser light

BEST MODES FOR CARRYING OUT THE INVENTION

A best mode for carrying out the present invention shall now be described in detail with reference to the attached drawings. In the description of the drawings, elements that are the same shall be provided with the same symbol and redundant description shall be omitted.

Figure 1:
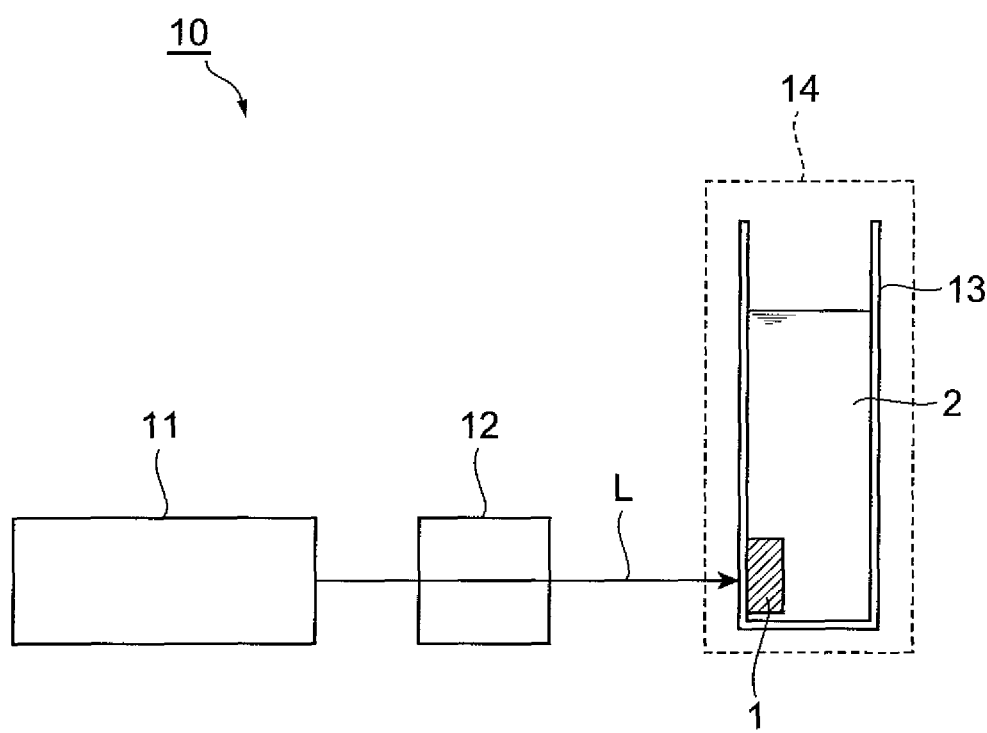
FIG. 1 is a configuration diagram of a microparticle dispersion liquid manufacturing apparatus 10 according to an embodiment.

FIG. 1 is a configuration diagram of a microparticle dispersion liquid manufacturing apparatus 10 according to an embodiment. As shown in FIG. 1, the microparticle dispersion liquid manufacturing apparatus 10 includes a laser light source 11, an irradiation light controller 12, a container 13, and a temperature controller 14, and is for manufacturing a liquid having microparticles, containing a poorly soluble drug and a dispersion stabilizer, dispersed in water.

The container 13 is for containing a liquid to be treated, is composed of a material enabling transmission of a laser light L output from the laser light source 11, and is preferably composed of quartz glass. The temperature controller 14 includes a constant temperature bath, a thermometer, and temperature control unit, and maintains the container 13, housed in the constant temperature bath, and the treated liquid, contained in an interior of the container 13, at a fixed temperature by feedback control by the thermometer and the temperature control unit. A portion of the constant temperature bath, through which the laser light L, output from the laser light source 11, passes, is configured as a transparent window. The laser light source 11 emits the laser light L toward the container 13 and preferably emits an infrared laser light L with a wavelength of no less than 900 nm. The irradiation light controller 12 adjusts both or either of an intensity and an irradiation duration of the laser light L emitted from the laser light source 11 and irradiated on the container 13.

Figure 2:
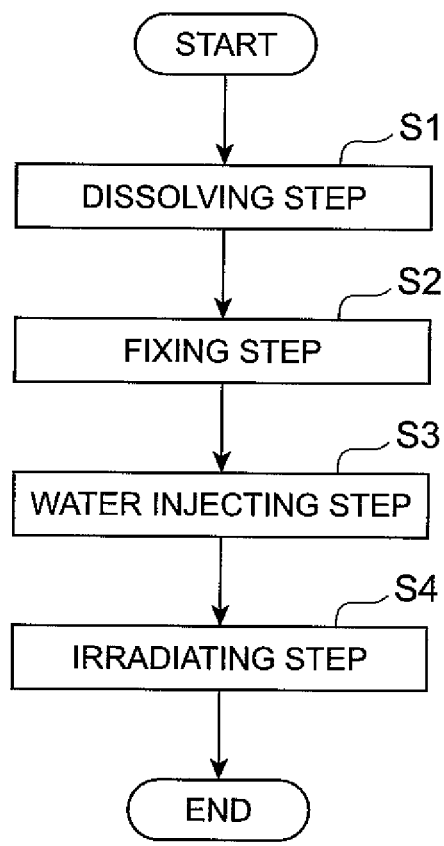
FIG. 2 is a flowchart for describing a microparticle dispersion liquid manufacturing method according to the embodiment.

An operation of the microparticle dispersion liquid manufacturing apparatus 10 according to the embodiment shall now be described along with a method for manufacturing a microparticle dispersion liquid according to the embodiment. FIG. 2 is a flowchart for describing the microparticle dispersion liquid manufacturing method according to the embodiment. With the microparticle dispersion liquid manufacturing method according to the embodiment, a liquid, having microparticles, containing a poorly soluble drug and a dispersion stabilizer, dispersed in water, is manufactured by successively carrying out a dissolving step S1, a fixing step S2, a water injecting step S3, and an irradiating step S4.

In the dissolving step S1, the poorly soluble drug and the dispersion stabilizer are dissolved in a volatile organic solvent in the container 13. The poorly soluble drug is a drug that hardly dissolves in water and although a solubility thereof is not restricted in particular, the solubility is preferably no more than 50 µg/mL at a temperature of 25° C. Commercially sold drugs, such as cyclosporin, tacrolimus, nifedipine, nicardipine hydrochloride, phenyloin, digitoxin, diazepam, nitrofurantoin, benoxaprofen, griseofulvin, sulfathiazole, piroxicam, carbamazepine, phenacetin, tolbutamide, theophylline, griseofulvin, chloramphenicol, paclitaxel, camptothecine, cisplatin, daunorubicin, methotrexate, mitomycin C, docetaxel, vincristine, amphotericin B, nystatin, ibuprofen, and clobetasone butyrate and other corticosteroids, and other new drug candidate substances in development can be cited as examples of the poorly soluble drug.

The dispersion stabilizer is preferably a high molecular weight polymer or a surfactant. The high molecular weight polymer is preferably a substance that is high in water solubility and is readily soluble in various organic solvents. Hydroxypropylmethylcellulose, methylcellulose, hydroxypropylcellulose, hydroxypropylmethylcellulose phthalate, hydroxypropylmethylcellulose acetate succinate, sodium carboxymethylcellulose, cellulose acetate phthalate, and other cellulose derivatives, agar, gelatin, sodium alginate, polyvinylpyrrolidone, aminoalkylmethacrylate copolymer, methacrylic acid copolymer, carboxyvinyl polymer, polyvinyl alcohol, polyethylene glycol, etc., can be cited as examples of the high molecular weight polymer. The surfactant is preferably of low toxicity, and sodium lauryl sulfate, cholic acid, deoxycholic acid, polyoxyethylene sorbitan fatty acid ester, etc., can be cited as examples.

As the organic solvent, methanol, ethanol, propanol, and other alcohols, acetone, acetonitrile, methyl acetate, ethyl acetate, diethyl ether, etc., can be cited as examples, and methanol, ethanol, propanol, and other alcohols are more preferable.

In the fixing step S2, following the dissolving step S1, the organic solvent contained in the solution obtained in the dissolving step S1 is eliminated by evaporation, and by the organic solvent elimination, a pellet-form residue 1 is obtained and this residue becomes fixed on an inner wall of the container 13. In the water injecting step S3 following the fixing step S2, water 2 is injected into the interior of the container 13. By this water injection, the residue 1, fixed on the inner wall of the container 13, becomes immersed in the water 2 (see FIG. 1).

Then in the irradiating step S4, following the water injecting step S3, the laser light L, emitted from the laser light source 11, is irradiated on the residue 1 fixed on the inner wall of the container 13, the residue 1 is thereby pulverized and made into microparticles, and a microparticle dispersion liquid, in which the microparticles are dispersed in the water 2, is thereby manufactured. The microparticles contain the poorly soluble drug and the dispersion stabilizer.

With the microparticle dispersion liquid manufacturing apparatus 10 according to the present embodiment or the microparticle dispersion liquid manufacturing method according to the present embodiment, because the laser light L is irradiated at high efficiency on the pellet-form residue 1 fixed on the inner wall of the container 13, the microparticle dispersion liquid can be manufactured at high efficiency in a short time. Because microparticles are formed even under adequately weak light irradiation such that laser ablation does not occur, the problem of drug degradation, etc., can be suppressed.

Microparticles, containing the poorly soluble drug and the dispersion stabilizer, are manufactured from the microparticle dispersion liquid manufactured as described above. Or, lyophilized microparticles are manufactured by lyophilizing the microparticle dispersion liquid. Furthermore, an orally administered formulation, containing the microparticle dispersion liquid, the microparticles, or the lyophilized microparticles, is manufactured, or an injection formulation, containing the microparticle dispersion liquid or a dispersion liquid, obtained by resuspending the microparticles or the lyophilized microparticles in water, is manufactured.

Preferably in the irradiating step S4, the laser light L is irradiated from outside a region of the inner wall of the container 13 on which the residue 1 is fixed as shown in FIG. 1 and the irradiated laser light L propagates in the order of the container 13, the residue 1, and the water 2. Microparticles are thereby formed near the interface of the residue 1 and the water 2 and these microparticles become immediately dispersed in the water 2. Because the laser light irradiation on the interface is constantly performed via the residue 1, even when a high concentration of the microparticles is contained in the water 2, the microparticle formation is not lowered in efficiency and the microparticles are formed at a fixed efficiency.

Preferably in the irradiating step S4, laser light L of a wavelength of no less than 900 nm is irradiated on the residue 1 from the laser light source 11. By the laser light L of such wavelength being irradiated on the residue 1, photodegradation of the drug contained in the residue 1 can be suppressed further. Also because the laser light L arrives at the interface via the residue 1 and the microparticles are formed at the interface, laser light L of a wavelength of low absorbance with respect to the residue 1 is preferably irradiated on the residue 1. Specifically, laser light L of a wavelength with which the absorbance with respect to the residue 1 is no more than 0.01 is preferably irradiated.

Preferably in the irradiating step S4, both or either of the intensity and the duration of light irradiation on the residue 1 are or is adjusted by the irradiation light controller 12, and in this case, it becomes possible to control a particle diameter of the microparticles formed by the light irradiation. Preferably during the light irradiation on the residue 1, the irradiated region or the interior of the container is maintained at a fixed temperature by the temperature controller 14, and in this case, the particle diameter of the microparticles formed by the light irradiation is stabilized.

Preferably a sealed container is used as the container 13, and the dissolving step S1, the fixing step S2, the water injecting step S3, and irradiating step S4 are performed in a sterilized state. Or the dissolving step S1 may be performed under a non-sterilized state and after filter sterilization of the solution, the fixing step S2, the water injecting step S3, and the irradiating step S4 may be performed in a sterilized state. That is, because the present embodiment provides a simple method of simply irradiating light from the exterior of the container 13, it can be put into practice even in a sealed container and an injectable product can also be manufactured readily in a sterilized state.

Figure 3:
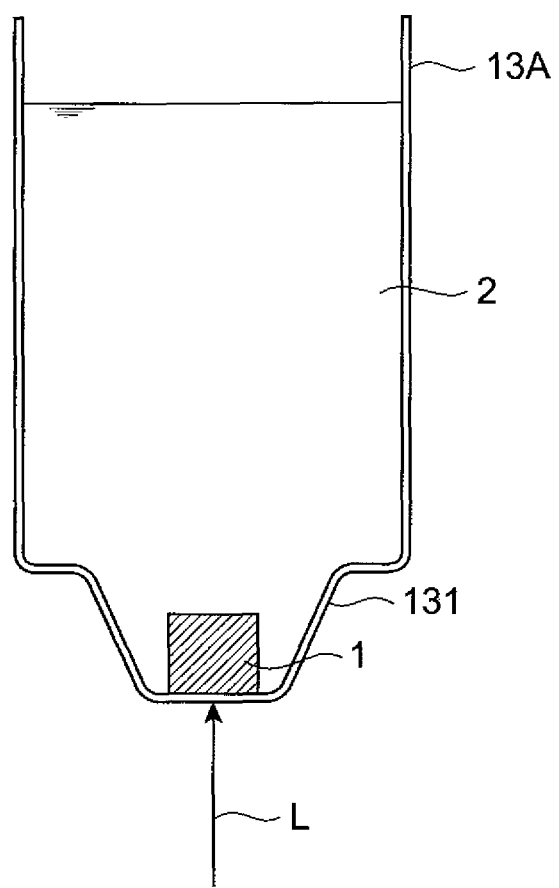
FIG. 3 is a configuration diagram of a modification example of a container 13 used in the microparticle dispersion liquid manufacturing apparatus 10 or the microparticle dispersion liquid manufacturing method according to the embodiment.

FIG. 3 is a configuration diagram of a modification example of the container 13 used in the microparticle dispersion liquid manufacturing apparatus 10 or the microparticle dispersion liquid manufacturing method according to the embodiment. A container 13A, which is the modification example of the container 13 shown in the figure, has a recess 131 in the inner wall for fixing the residue 1. The residue 1 can thereby be positioned at the recess 131, which is a constantly fixed position with respect to the outer wall of the container 13A, and adjustment of a light irradiating position of the laser light L is facilitated. The recess 131 is preferably round as illustrated because it is then strong against distortion.

Figure 4:
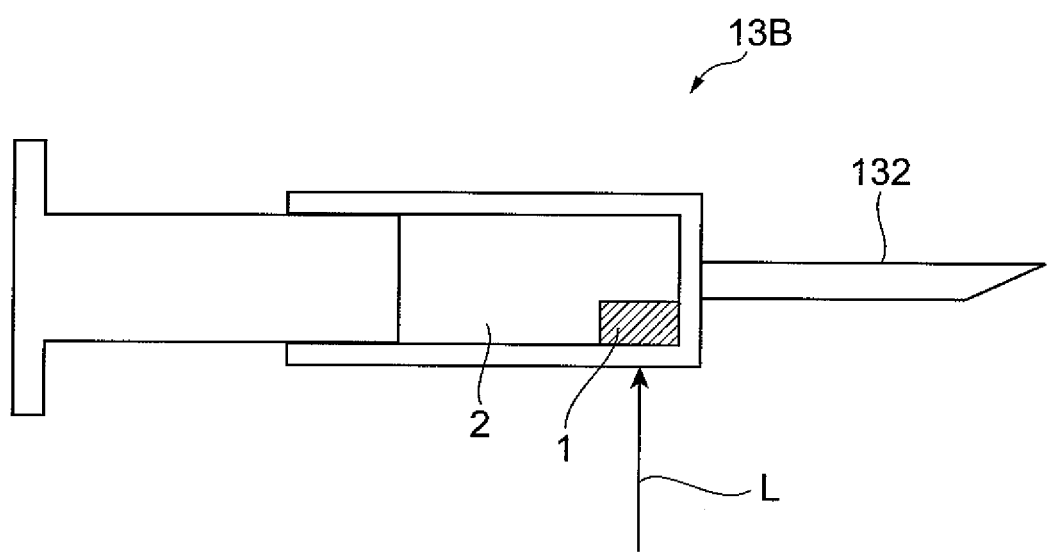
FIG. 4 is a configuration diagram of another modification example of the container 13 used in the microparticle dispersion liquid manufacturing apparatus 10 or the microparticle dispersion liquid manufacturing method according to the embodiment.

FIG. 4 is a configuration diagram of another modification example of the container 13 used in the microparticle dispersion liquid manufacturing apparatus 10 or the microparticle dispersion liquid manufacturing method according to the embodiment. A container 13B, which is the modification example of the container 13 shown in the figure, has a function of a syringe. The container 13B includes an injection needle 132 and this provides a merit of enabling rapid injection of the microparticle dispersion liquid immediately after manufacture. A recess for fixing the residue 1 may also be provided in an inner wall of the syringe as in the container 13A of the above-described modification example.

Example 1

More specific examples of the microparticle dispersion liquid manufacturing apparatus or the microparticle dispersion liquid manufacturing method according to the embodiment shall now be described.

Example 1 shall be described first. In Example 1, a microparticle dispersion liquid of an immunosuppressant, cyclosporin A (hereinafter referred to as "CsA"), which is a poorly soluble drug, was prepared. CsA bulk powder (10 mg) as the poorly soluble drug and polyvinylpyrrolidone (50 mg) and sodium lauryl sulfate (2 mg) as dispersion stabilizers were placed in a test tube and dissolved in ethanol (1 mL), which is a volatile organic solvent. The ethanol was dried under reduced pressure conditions to obtain a mixture (residue) of the drug and the dispersion stabilizers. The mixture thus obtained was hermetically sealed upon adding water.

Nd:YAG pulse laser light was irradiated from a side of the test tube onto the mixture inside the test tube. The irradiation conditions were: a wavelength of 1064 nm; an irradiation light intensity of 0.61 $J/cm^2$/pulse; a pulse width of 5 to 7 ns; and a repetition frequency of 10 Hz. After 10 minutes of irradiation, a uniformly cloudy dispersion liquid was obtained upon shaking gently. In the present example, all operations were carried out under room temperature (20° C.).

Figure 5:
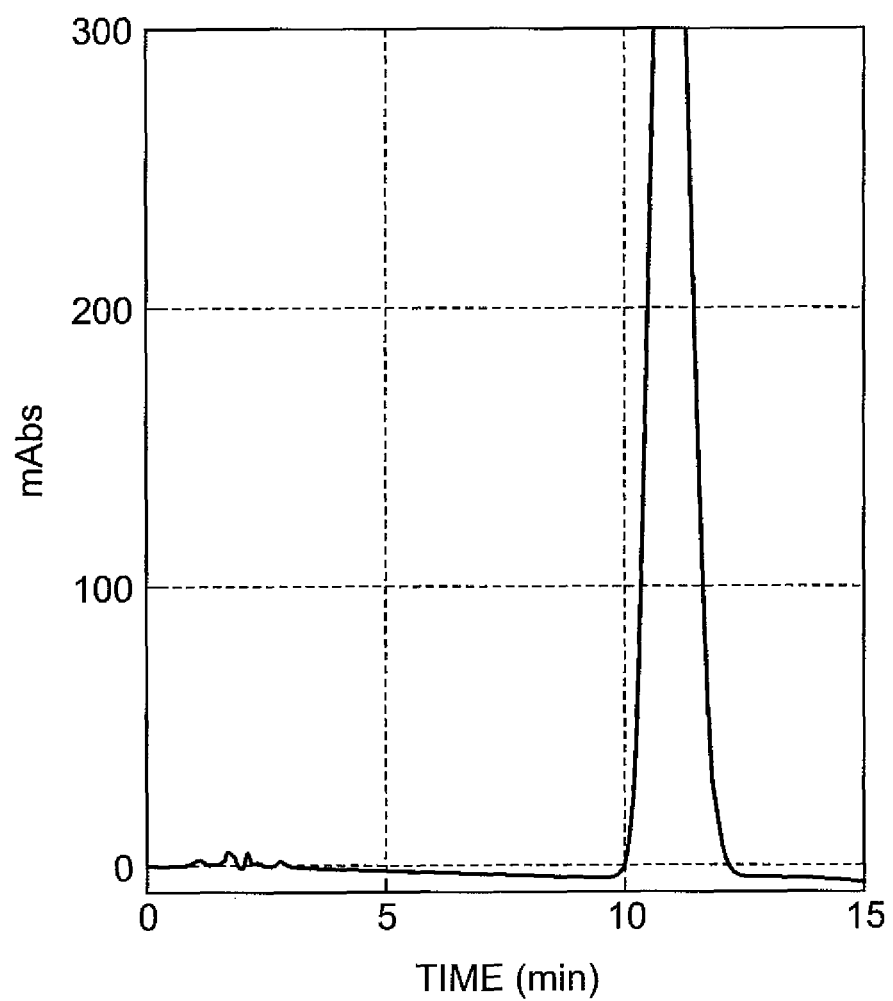
FIG. 5 is an HPLC chart of a microparticle dispersion liquid obtained in Example 1.

A CsA amount contained in the dispersion liquid obtained was quantified using high performance liquid chromatography (hereinafter referred to as "HPLC") and by measuring an absorbance at a wavelength of 210 nm. FIG. 5 is an HPLC chart of the microparticle dispersion liquid obtained in Example 1. ODS-C18 (manufactured by Tosoh Corp.) was used as a separation substrate and acetonitrile-isopropanol-water (2:5:3) was used as a mobile phase to carry out the chromatography at a temperature of 50° C. CsA was eluted at a position of approximately 11 minutes, and as a result of comparing and calculating the CsA amount in the sample based on a peak area obtained by measuring a reference preparation, the CsA amount in the microparticle dispersion liquid was found to be 9.15±0.32 mg/mL (n=3). It was thus possible to prepare a microparticle dispersion liquid with an adequately high concentration in comparison to a solubility (23 μg/ml) in water. Increase in impurity peaks due to laser irradiation was not seen on the HPLC chart.

Figure 6:
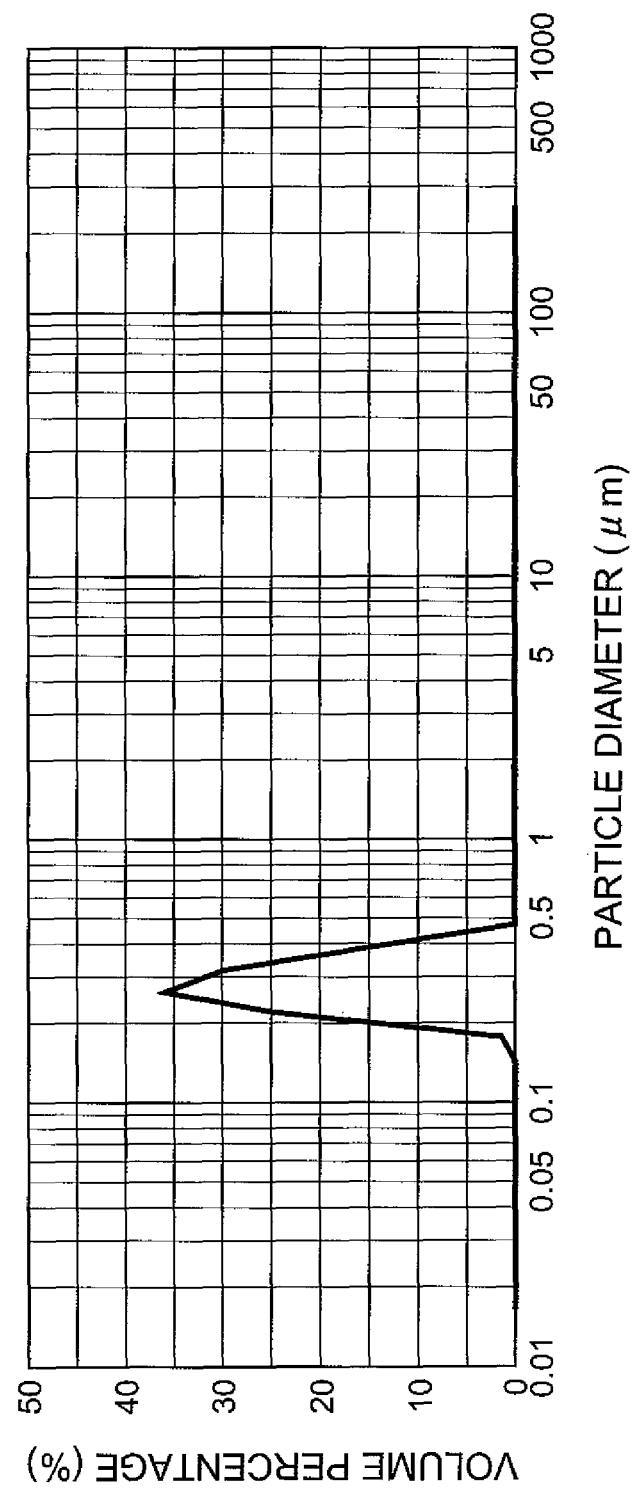
FIG. 6 is a diagram of a particle size distribution of microparticles contained in the microparticle dispersion liquid obtained in Example 1.

FIG. 6 is a diagram of a particle size distribution of the microparticles contained in the microparticle dispersion liquid obtained in Example 1. SALD-7000 (manufactured by Shimadzu Corp.) was used as a measuring apparatus for particle diameter measurement. A particle size distribution having a particle diameter range of 150 to 450 nm and a peak at 250 nm was obtained. The dispersion liquid is thus considered to be a uniform microparticle suspension liquid of uniform particle size.

Figure 7:
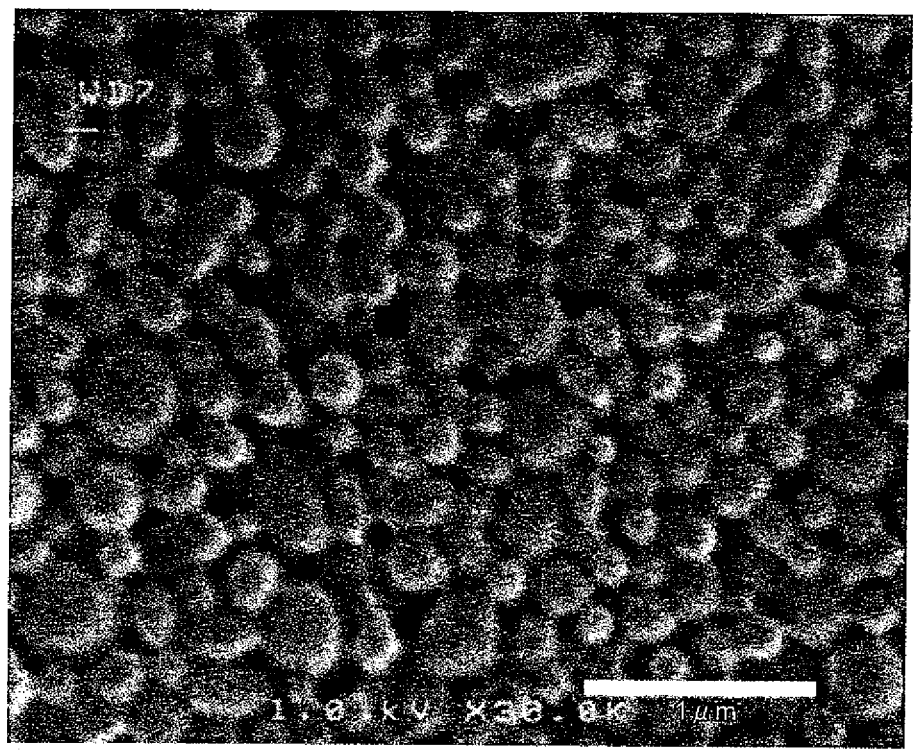
FIG. 7 is an electron micrograph of the microparticles contained in the microparticle dispersion liquid obtained in Example 1.

FIG. 7 is an electron micrograph of the microparticles contained in the microparticle dispersion liquid obtained in Example 1. A scanning electron microscope S4200 (manufactured by Hitachi, Ltd.) was used as a measuring apparatus. As can be seen from the photograph, the microparticles have a spherical shape and numerous microparticles with a particle diameter of approximately 200 to 300 nm were observed. This matches the particle size distribution data of FIG. 6 and the microparticles are thus considered as being a uniform assembly of microparticles.

As described above, it was possible to prepare a microparticle dispersion, in which CsA microparticles of uniform particle diameter, are dispersed. It was also possible to prepare microparticle dispersion liquids of different particle diameters by varying the liquid phase temperature during laser irradiation, the irradiation intensity, and the irradiation duration (refer to the following examples). Sedimentation was hardly noted even when the dispersion liquids obtained were left to stand still at room temperature for several days. Furthermore, lyophilization was possible, and significant differences in the particle size distribution and the electron microscopy image were not seen between the state before lyophilization and a resuspended dispersion liquid.

Example 2

Figure 8:
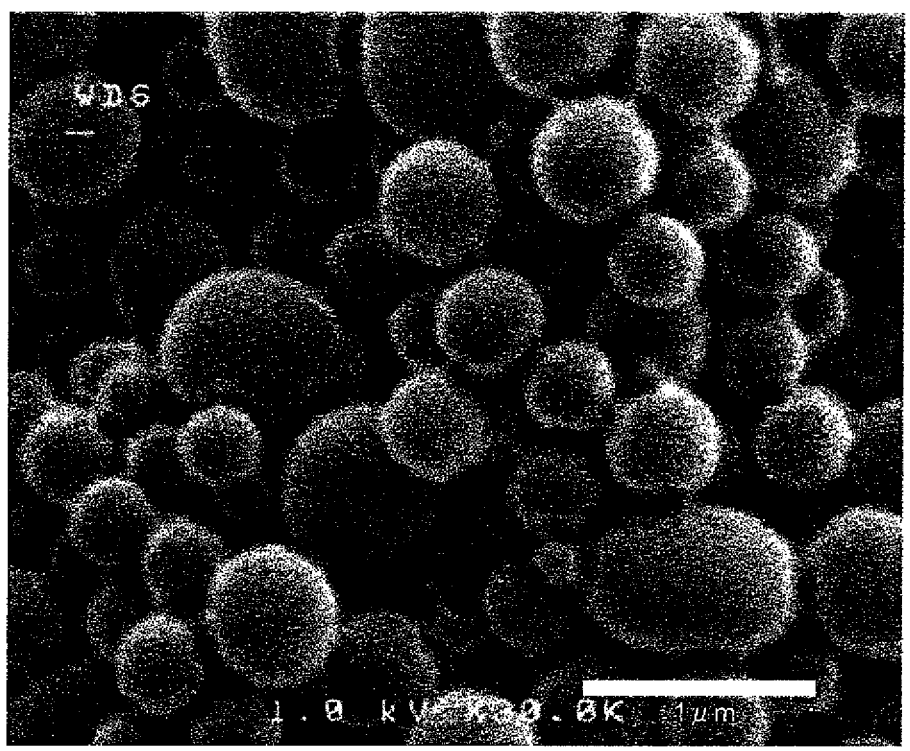
FIG. 8 is an electron micrograph of microparticles contained in a microparticle dispersion liquid obtained in Example 2.

Example 2 shall now be described. In Example 2, poloxamer 407 (50 mg) was used as the dispersion stabilizer. Other manufacturing conditions and the microscopic observation conditions are the same as those of Example 1. FIG. 8 is an electron micrograph of microparticles contained in a microparticle dispersion liquid obtained in Example 2. As can be seen from the photograph, the microparticles have a spherical shape and numerous microparticles with a particle diameter of no more than micrometer size were observed.

Example 3

Figure 9:
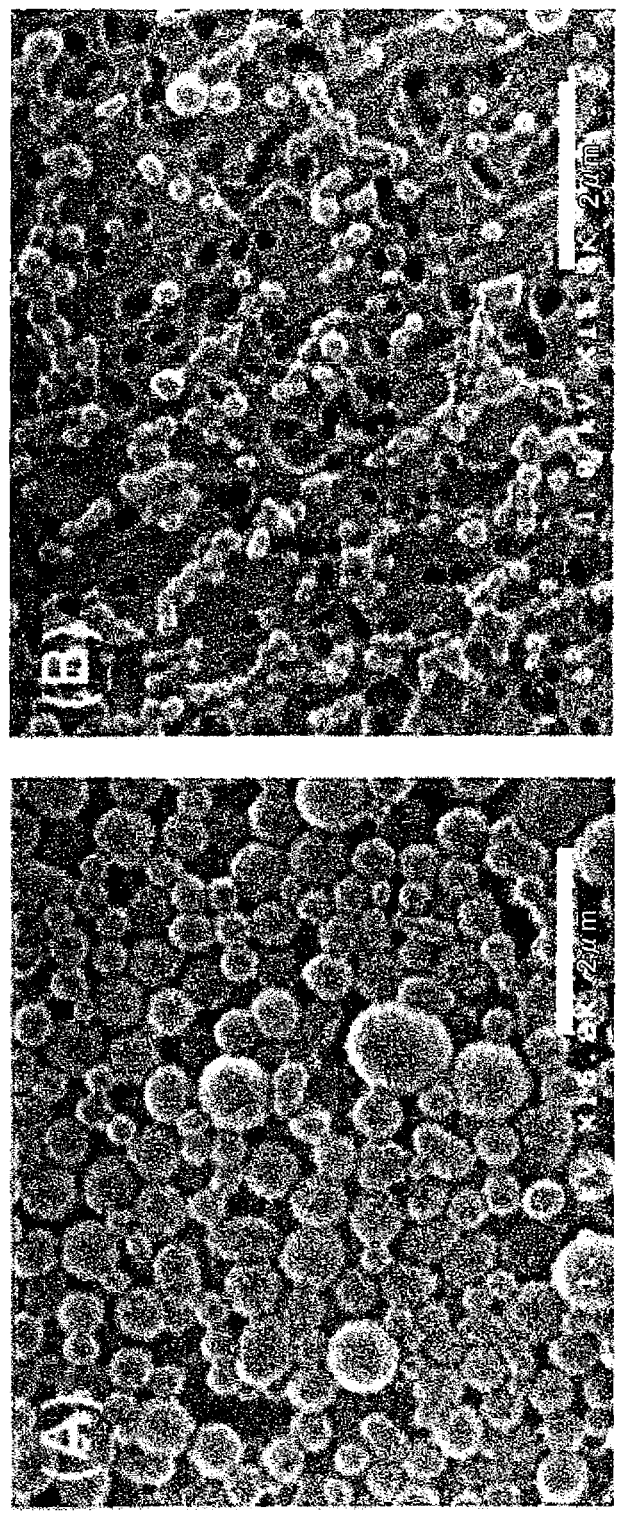
FIG. 9 shows electron micrographs of microparticles contained in microparticle dispersion liquids obtained in Example 3.

Example 3 shall now be described. In Example 3, the intensity of the laser light irradiated on the mixture (residue) inside the test tube was set to 0.30 or 0.61 $J/cm^2$/pulse. Other manufacturing conditions and the microscopic observation conditions are the same as those of Example 1. FIG. 9 shows electron micrographs of microparticles contained in microparticle dispersion liquids obtained in Example 3. FIG. 9A is an electron micrograph of the microparticles in the case of the irradiation light intensity of 0.30 $J/cm^2$/pulse, and FIG. 9B is an electron micrograph of the microparticles in the case of the irradiation light intensity of 0.61 $J/cm^2$/pulse. As can be seen from the photographs, the microparticles have a spherical shape, the particle diameter varies according to the irradiation intensity and the particle diameter is smaller in the case of lower irradiation light intensity. From these results, it is considered that the higher the irradiation light intensity, the larger the particle diameter of the microparticles formed.

Example 4

Figure 10:
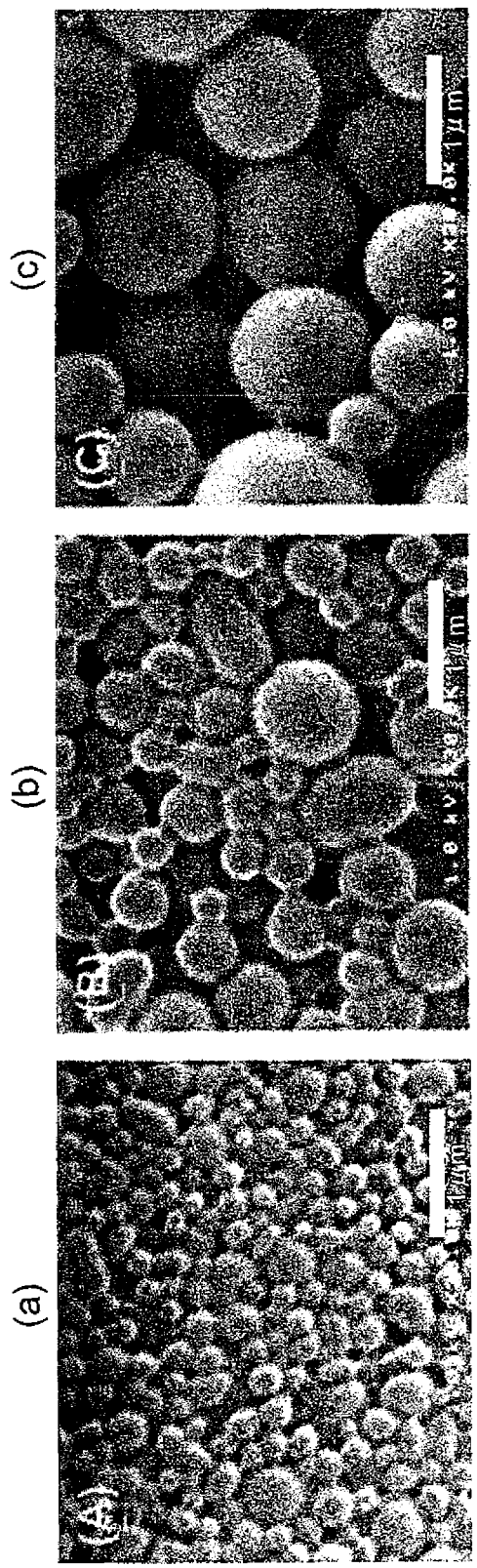
FIG. 10 shows electron micrographs of microparticles contained in microparticle dispersion liquids obtained in Example 4.

Example 4 shall now be described. In Example 4, the duration of irradiation of the laser light on the mixture (residue) inside the test tube was set to 10, 60, or 180 minutes. Other manufacturing conditions and the microscopic observation conditions are the same as those of Example 1. FIG. 10 shows electron micrographs of microparticles contained in microparticle dispersion liquids obtained in Example 4. FIG. 10A is an electron micrograph of the microparticles in the case of the irradiation duration of 10 minutes, FIG. 10B is an electron micrograph of the microparticles in the case of the irradiation duration of 60 minutes, and FIG. 10C is an electron micrograph of the microparticles in the case of the irradiation duration of 180 minutes. As can be seen from the photographs, the microparticles have a spherical shape and the particle diameter varies according to the irradiation duration. Whereas with the sample for the irradiation duration of 10 minutes (FIG. 10A), there is a large number of microparticles with a particle diameter of 200 to 500 nm, with the sample for the irradiation duration of 60 minutes (FIG. 10B) there is a large number of microparticles with a particle diameter of 500 to 1 µm, and with the sample for the irradiation duration of 180 minutes (FIG. 10C), there is a large number of microparticles with a particle diameter exceeding 1 µm. From these results, it is considered that the longer the irradiation duration, the larger the particle diameter of the microparticles formed.

Example 5

Figure 11:
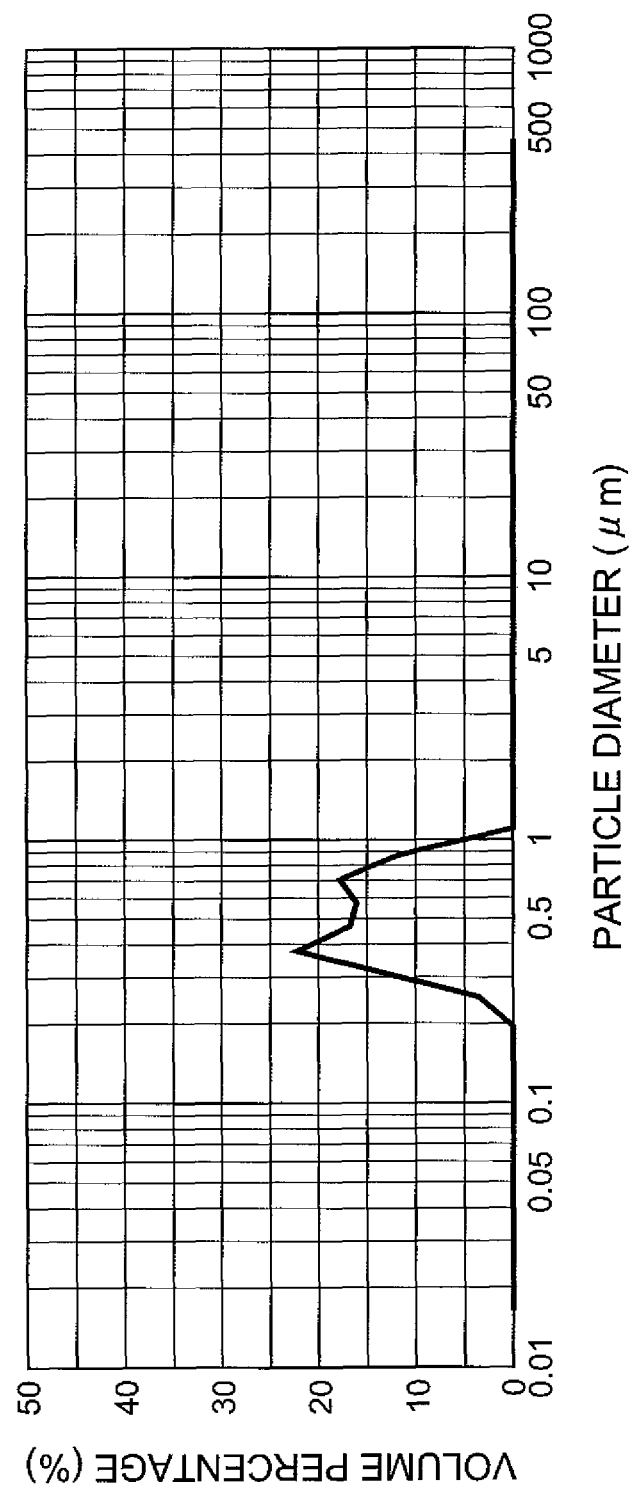
FIG. 11 is a diagram of a particle size distribution of microparticles contained in a microparticle dispersion liquid obtained in Example 5.
Figure 12:
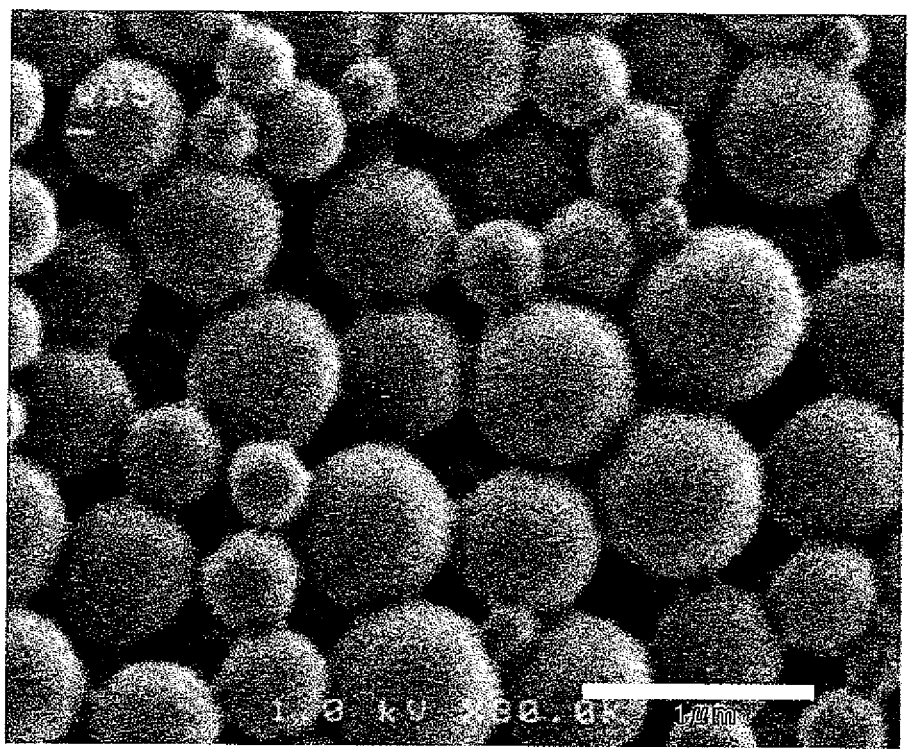
FIG. 12 is an electron micrograph of the microparticles contained in the microparticle dispersion liquid obtained in Example 5.

Example 5 shall now be described. In Example 5, an anti-inflammatory drug, clobetasone butyrate, was used as the poorly soluble drug and a microparticle dispersion liquid of clobetasone butyrate was prepared. Other manufacturing conditions, particle size distribution measuring conditions and the microscopic observation conditions are the same as those of Example 1. FIG. 11 is a diagram of a particle size distribution of microparticles contained in the microparticle dispersion liquid obtained in Example 5. FIG. 12 is an electron micrograph of the microparticles contained in the microparticle dispersion liquid obtained in Example 5. As can be understood from the diagram and the photograph, the microparticles have a spherical shape, numerous microparticles with a particle diameter of no more than micrometer size were observed, the microparticles in the dispersion liquid are present within a range of 200 nm to 1 µm, and the dispersion liquid is thus considered to be a uniform microparticle suspension liquid of uniform particle size.

Example 6

Figure 13:
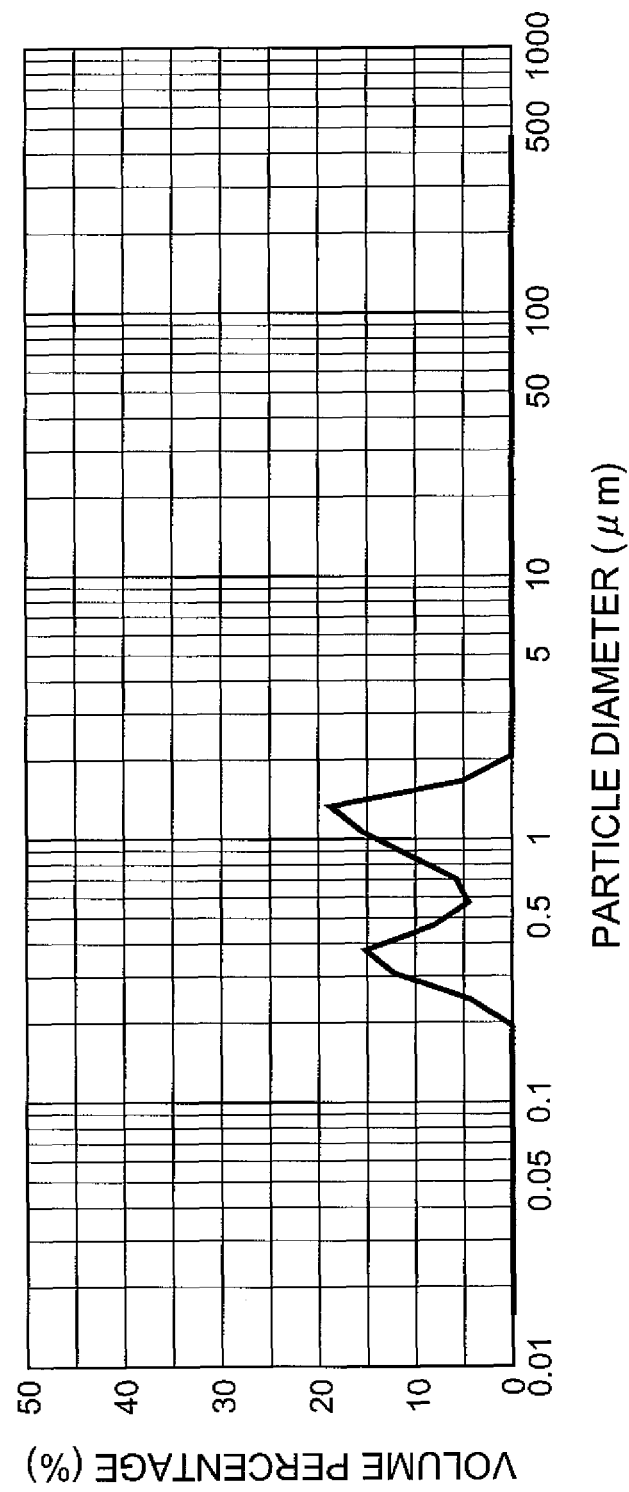
FIG. 13 is a diagram of a particle size distribution of microparticles contained in a microparticle dispersion liquid obtained in Example 6.

Example 6 shall now be described. In Example 6, an anti-epileptic drug, nifedipine, was used as the poorly soluble drug and a microparticle dispersion liquid of nifedipine was prepared. Other manufacturing conditions and the particle size distribution measuring conditions are the same as those of Example 1. FIG. 13 is a diagram of a particle size distribution of microparticles contained in the microparticle dispersion liquid obtained in Example 6. As can be understood from the diagram, the microparticles in the dispersion liquid are present within a range of 200 nm to 2 µm and the dispersion liquid is considered to have particle diameter peaks at 400 nm and 1.2 µm.

Example 7

Figure 14:
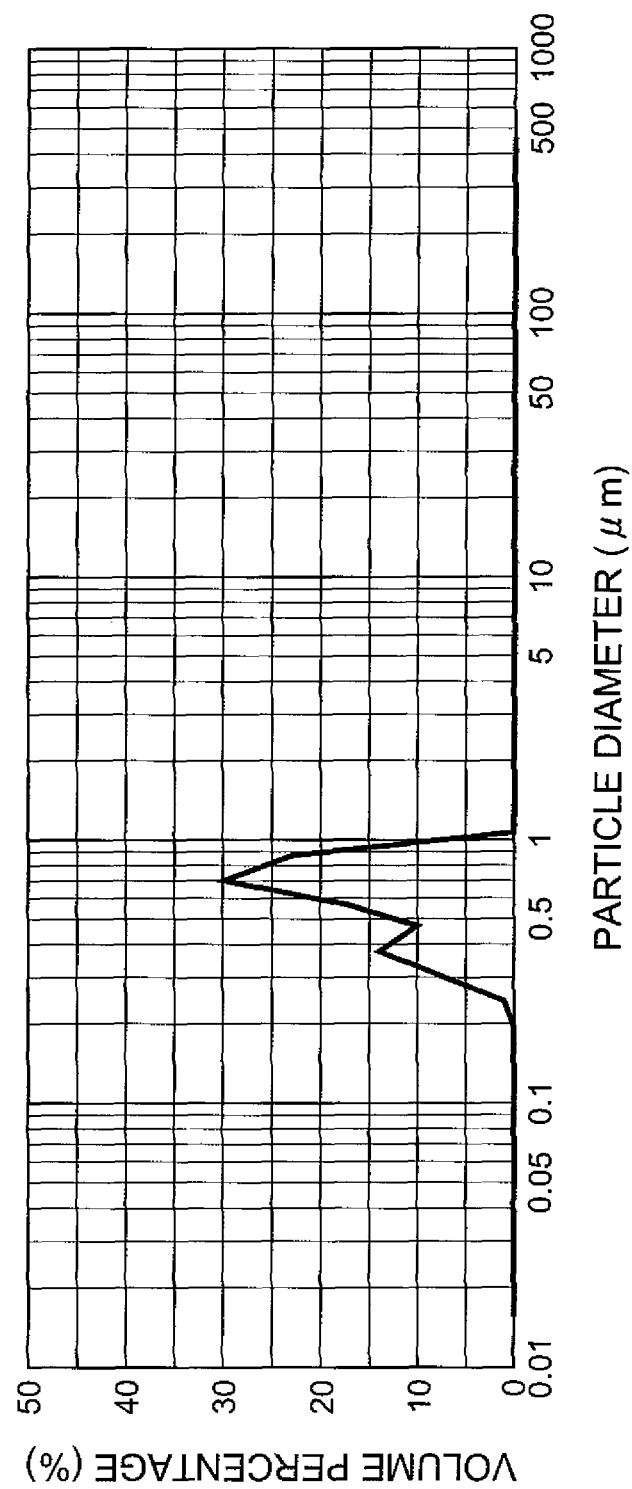
FIG. 14 is a diagram of a particle size distribution of microparticles contained in a microparticle dispersion liquid obtained in Example 7.

Example 7 shall now be described. In Example 7, an anti-inflammatory drug, ibuprofen, was used as the poorly soluble drug and a microparticle dispersion liquid of ibuprofen was prepared. Other manufacturing conditions and the particle size distribution measuring conditions are the same as those of Example 1. FIG. 14 is a diagram of a particle size distribution of microparticles contained in the microparticle dispersion liquid obtained in Example 7. As can be understood from the diagram, the microparticles in the dispersion liquid are present within a range of 250 nm to 1 µm, and the dispersion liquid is thus considered to be a uniform microparticle suspension liquid of uniform particle size having a particle diameter peak at 700 nm.

INDUSTRIAL APPLICABILITY

The present invention can be used in development of new medical drugs, etc.

The invention claimed is:

1. A microparticle dispersion liquid manufacturing method comprising:
    a dissolving step of dissolving a poorly soluble drug and a dispersion stabilizer in a volatile organic solvent;
    a fixing step of performing elimination by evaporation of the organic solvent, contained in a solution obtained in the dissolving step, and fixing a residue, obtained by the organic solvent elimination, at a fixed position on an inner wall of a syringe;
    a water injecting step of injecting water into an interior of the syringe after the fixing step such that the residue remains fixed on the inner wall of the syringe and is immersed in the water; and
    an irradiating step of irradiating light on the residue fixed on the inner wall of the syringe after the water injecting step to manufacture a liquid having microparticles, containing the poorly soluble drug and the dispersion stabilizer, dispersed in water,
    wherein in the irradiating step, light is irradiated from outside a region of the inner wall of the syringe on which the residue is fixed, and the irradiated light is made to propagate in an order of the syringe, the residue, and the water.

2. The microparticle dispersion liquid manufacturing method according to claim 1, wherein light of a wavelength of no less than 900 nm is irradiated on the residue in the irradiating step.

3. The microparticle dispersion liquid manufacturing method according to claim 2, wherein light of a wavelength of low absorbance with respect to the residue is irradiated in the irradiating step.

4. The microparticle dispersion liquid manufacturing method according to claim 1, wherein both or either of an intensity and a duration of light irradiation on the residue are or is adjusted in the irradiating step to control a particle diameter of the microparticles.

5. The microparticle dispersion liquid manufacturing method according to claim 1, wherein the irradiated region or the interior of the syringe is maintained at a fixed temperature during light irradiation on the residue in the irradiating step.

6. The microparticle dispersion liquid manufacturing method according to claim 1, wherein
    the dissolving step, the fixing step, the water injecting step, and the irradiating step are performed in a sterilized state.

7. The microparticle dispersion liquid manufacturing method according to claim 1, wherein the dispersion stabilizer is a high molecular weight polymer or a surfactant.

8. The microparticle dispersion liquid manufacturing method according to claim 1, wherein the organic solvent is a low toxicity alcohol.

* * * * *

UNITED STATES PATENT AND TRADEMARK OFFICE
CERTIFICATE OF CORRECTION

PATENT NO.        : 8,663,702 B2                                                         Page 1 of 1
APPLICATION NO. : 12/295666
DATED             : March 4, 2014
INVENTOR(S)       : Takebe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 943 days.

Signed and Sealed this

Twenty-ninth Day of September, 2015

Michelle K. Lee
*Director of the United States Patent and Trademark Office*